(12) United States Patent
AE et al.

(10) Patent No.: US 8,586,737 B2
(45) Date of Patent: Nov. 19, 2013

(54) PROCESS OF A QUATERNARY AMMONIUM SALT USING PHOSPHATE

(75) Inventors: Nobuyuki AE, Osaka (JP); Yuji Fujiwara, Osaka (JP)

(73) Assignee: Dainippon Sumitomo Pharma Co., Ltd., Osaka-shi, Osaka (JP)

( * ) Notice: Subject to any disclaimer, the term of this patent is extended or adjusted under 35 U.S.C. 154(b) by 191 days.

(21) Appl. No.: 13/093,985

(22) Filed: Apr. 26, 2011

(65) Prior Publication Data

US 2011/0263848 A1  Oct. 27, 2011

Related U.S. Application Data

(60) Provisional application No. 61/327,804, filed on Apr. 26, 2010.

(51) Int. Cl.
| | |
|---|---|
| *C07D 471/10* | (2006.01) |
| *C07D 487/10* | (2006.01) |
| *C07D 209/48* | (2006.01) |
| *C07D 209/76* | (2006.01) |
| *C07D 401/08* | (2006.01) |
| *C07D 413/12* | (2006.01) |
| *C07D 413/14* | (2006.01) |

(52) U.S. Cl.
USPC .......... 544/231; 544/3; 544/368; 546/16; 546/17

(58) Field of Classification Search
None
See application file for complete search history.

(56) References Cited

U.S. PATENT DOCUMENTS

| | | | |
|---|---|---|---|
| 5,182,280 | A | 1/1993 | Cuberes-Altisent et al. |
| 5,532,372 | A | 7/1996 | Saji et al. |
| 2007/0049750 | A1 | 3/2007 | Siggel et al. |
| 2011/0003994 | A1 | 1/2011 | Maruyama |
| 2011/0263847 | A1 | 10/2011 | AE et al. |

FOREIGN PATENT DOCUMENTS

| | | |
|---|---|---|
| EP | 0464846 A1 | 1/1992 |
| JP | 5017440 A | 1/1993 |
| JP | 8-333368 A | 12/1996 |
| JP | 2800953 B2 | 9/1998 |
| WO | WO 2007/027649 A1 | 3/2007 |
| WO | 2011/002103 A2 | 1/2011 |
| WO | 2011/136383 A1 | 11/2011 |

OTHER PUBLICATIONS

International Preliminary Report on Patentability, dated Oct. 30, 2012, International Application No. PCT/JP2011/060571.
Qi Sun et al., "Unique spirocyclopiperazinium salt III: Further investigation of monospirocyclopiperazinium (MSPZ) salts as potential analgesics", Bioorganic & Medicinal Chemistry Letters, vol. 17, 2007, pp. 6245-6249.
Translation of JP 2003-160583, (2003).
Translation of JP 2006-169155, (2006).
Translation of JP 2006-169154, (2006).
Supplementary European Search Report dated Apr. 13, 2013 issued in European Application 11775165.1.
Joseph P. Yevich et al., "Synthesis and Biological Evaluation of 1-(1,2-Benzisothiazol-3-yl)- and (1,2-Benzisoxazol-3-yl)piperazine Derivatives as Potential Antipsychotic Agents", Journal of Medicinal Chemistry, vol. 29, No. 3, pp. 359-369, Jan. 1, 1986.

*Primary Examiner* — Emily Bernhardt
(74) *Attorney, Agent, or Firm* — Fitch, Even Tabin & Flannery, LLP

(57) ABSTRACT

The present invention relates to a novel process for preparing quaternary ammonium salt derivatives.

26 Claims, No Drawings

PROCESS OF A QUATERNARY AMMONIUM SALT USING PHOSPHATE

CROSS REFERENCE TO RELATED APPLICATION

This application is a utility application and claims the benefit of U.S. Provisional Application No. 61/327,804, filed Apr. 26, 2010 the complete disclosure of which is incorporated herein by reference.

TECHNICAL FIELD

The present invention relates to a process for preparing quaternary ammonium salt derivatives.

BACKGROUND ART

An imide derivative or a salt thereof whose typical example is a compound of formula (8) mentioned later or an acid addition salt thereof is known to be useful as a medicament for treating schizophrenia, senile psychiatric disorder, bipolar disorder, neurosis, etc. (Patent Reference 1). And, some processes for preparing an imide derivative of the following formula (I):

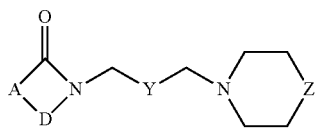
(I)

wherein A is optionally substituted $C_{2-4}$ alkylene group or other, D is carbonyl group or other, Y is optionally substituted $C_{1-2}$ alkylene group, Z is optionally substituted imino group or other
are also reported. For example, Patent Reference 2 discloses a process for preparing the imide derivative of the above-mentioned formula (I) which comprises reacting a compound of formula (II):

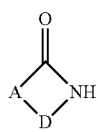
(II)

wherein A is optionally substituted $C_{2-4}$ alkylene group or other, and D is carbonyl group or other, and
a quaternary ammonium salt of formula (III):

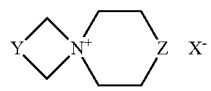
(III)

wherein Y is optionally substituted $C_{1-2}$ alkylene group, Z is optionally substituted imino group or other, $X^-$ is a counter-anion
in the presence of a solid inorganic base and water.

In addition, Patent Reference 3 discloses that the compound of formula (III) can be prepared by reacting a compound of formula (IV):

(IV)

wherein Z is optionally substituted imino group or other, and a compound of formula (V):

(V)

wherein X is a group which can become the above counter-anion $X^-$ after cleavage, and Y is optionally-substituted $C_{1-2}$ alkylene group in the presence of potassium carbonate whose specific surface area is less than 1.8 m²/g.

Furthermore, Patent Reference 4 discloses a process for preparing the compound of formula (III) which comprises reacting the compound of formula (IV) and the compound of formula (V) in an organic solvent in the presence of potassium carbonate whose mean particle size (50% D) is not more than 200 μm.

However, these processes have some problems on the preparing processes, for example, the product of formula (I) contains a by-product (hereinafter, referred to as "by-product (R)"), or the reaction time of the preparing processes is unstable. Such by-product (R) might cause the quality loss of the imide compound of formula (I), hence it is necessary to remove the by-product through a purification. Thus, it has been desired to further reduce the producing of by-product (R) and stabilize the reaction time from the viewpoint of the yield of the product and the production cost.

PRIOR ART

Patent Reference

[Patent Reference 1] JP 2800953 B
[Patent Reference 2] JP 2003-160583 A
[Patent Reference 3] JP 2006-169155 A
[Patent Reference 4] JP 2006-169154 A

DISCLOSURE OF INVENTION

Problem to be Solved by the Invention

Under the situation, the present inventors have extensively studied to reduce the producing of by-product (R) and then have found that the cause of producing by-product (R) is potassium carbonate which is used in the reaction of compound (IV) and compound (V) as a base. And, the inventors have further extensively studied other bases instead of potassium carbonate which has been understood as an optimal base in the reaction process and then have found that the producing of by-product (R) can be reduced by using dibasic potassium phosphate with a small amount of water as a base instead of potassium carbonate in the reaction between the following compound of formula (1) and the following compound of formula (2), and the improved process enable the reaction time to be stabilized. Based upon the new findings, the present invention has been completed.

Means to Solve the Problem

The present inventions are as follows.

Term 1:

A process for preparing a quaternary ammonium salt of formula (4):

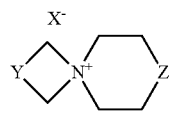
(4)

wherein

X is halogen atom, $C_{1-6}$ alkylsulfonyloxy group, or $C_{6-10}$ arylsulfonyloxy group, and $X^-$ is a counteranion thereof, Y is a substituent of the following formula (3a) or (3b):

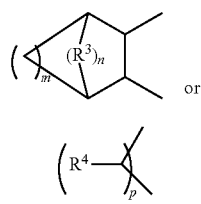

wherein $R^3$ is independently methylene or oxygen atom; $R^4$ is independently $C_{1-6}$ alkyl group, $C_{1-6}$ alkoxy group, or hydroxy group; m and n are independently 0, 1, 2, or 3; and p is 1 or 2, and Z is =N—$R^1$ or =CH—$R^2$ wherein $R^1$ is $C_{1-6}$ alkyl group, $C_{3-7}$ cycloalkyl group, $C_{5-7}$ cycloalkenyl group, $C_{6-10}$ aryl group, or 5- to 10-membered monocyclic or bicyclic heteroaryl group; $R^2$ is $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, or 5- to 10-membered monocyclic or bicyclic heteroarylthio group, comprising reacting a compound of formula (1):

(1)

wherein Z is as defined above with 1 to 2 mole of a compound of formula (2):

(2)

wherein X is independently selected from the above-defined ones, and Y is as defined above, per one mole of the compound of formula (1)

in the presence of 1 to 5 mole of a phosphate per one mole of the compound of formula (1) and 0.01 to 0.1 part by weight of water per one part by weight of the phosphate.

Term 2:

The process of Term 1 wherein X is independently $C_{1-6}$ alkylsulfonyloxy group, or $C_{6-10}$ arylsulfonyloxy group.

Term 3:

The process of Term 2 wherein X is methanesulfonyloxy group.

Term 4:

The process of any one of Terms 1 to 3 wherein Y is the substituent of formula (3a).

Term 5:

The process of Term 4 wherein m is 2 and n is 0.

Term 6:

The process of any one of Terms 1 to 5 wherein Z is =N—$R^1$.

Term 7:

The process of Term 6 wherein $R^1$ is 5- to 10-membered monocyclic or bicyclic heteroaryl group.

Term 8:

The process of Term 7 wherein $R^1$ is 1,2-benzisothiazol-3-yl.

Term 9:

The process of any one of Terms 1 to 8 wherein the phosphate is dibasic potassium phosphate.

Term 10:

The process of any one of Terms 1 to 9 wherein the phosphate is 1 to 3 mole per one mole of the compound of formula (1).

Term 11:

The process of any one of Terms 1 to 10 wherein the amount of water is 0.01 to 0.05 part by weight per one part by weight of the phosphate.

Term 12:

The process of any one of Terms 1, 9 to 11 wherein the compound of formula (1) is

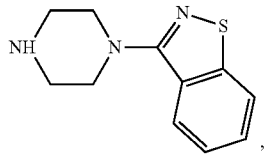

the compound of formula (2) is

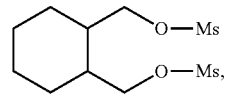

and the quaternary ammonium salt of formula (4) is

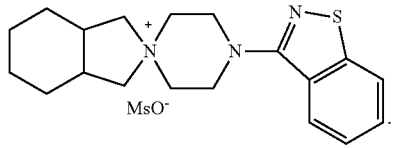 [SMILES: "MsO-" ; c1ccc2c(N3CC[N+]4(CC3)CC3CCCCC3C4)nsc2c1]

Term 13:
A process for preparing a compound of formula (8):

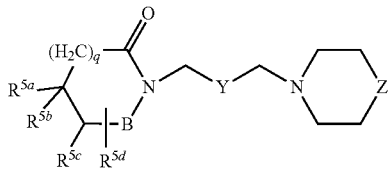

(8)

wherein
B is carbonyl group or sulfonyl group,
$R^{5a}, R^{5b}, R^{5c}$, and $R^{5d}$ are independently hydrogen atom or $C_{1-4}$ alkyl group, alternatively $R^{5a}$ and $R^{5b}$, or $R^{5a}$ and $R^{5c}$ may be taken together to form a hydrocarbon ring, or $R^{5a}$ and $R^{5c}$ may be taken together to form an aromatic hydrocarbon ring, wherein the hydrocarbon ring may be bridged with $C_{1-4}$ alkylene or oxygen atom wherein the $C_{1-4}$ alkylene and the hydrocarbon ring may be substituted with at least one $C_{1-4}$ alkyl,
q is 0 or 1, and
Y and Z are as defined in Term 1,
comprising reacting the quaternary ammonium salt (4) prepared according to any one of claims 1 to 12 with the following compound (7):

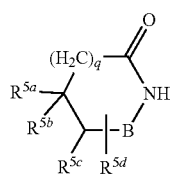

(7)

wherein B, $R^{5a}$, $R^{5b}$, $R^{5c}$, $R^{5d}$, and q are as defined above, in the presence of a solid inorganic base.

Term 14:
The process of Term 13 wherein B is carbonyl group.

Term 15:
The process of Term 13 or 14 wherein $R^{5a}$ and $R^{5c}$ are taken together to form a hydrocarbon ring which may be bridged with $C_{1-4}$ alkylene, and $R^{5b}$ and $R^{5d}$ are hydrogen atom.

Term 16:
The process of Term 15 wherein Compound (7) is the following compound of formula (7b):

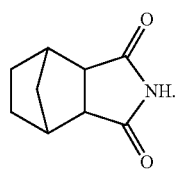

(7b)

Term 17:
The process of any one of Terms 13 to 16 wherein Compound (8) is (3aR,4S,7R,7aS)-2-{(1R,2R)-2-[4-(1,2-benzisothiazol-3-yl)-piperazin-1-ylmethyl]cyclohexyl-methyl}hexahydro-4,7-methano-2H-isoindole-1,3-dione.

Effect of the Invention

According to the present invention, the production of by-product (R) can be held down because the reaction does not include potassium carbonate. In addition, the reaction is carried out with a small amount of water, thereby unfavorable variation of the reaction time caused by such heterogeneous reaction medium can be stabilized. Accordingly, the present reaction can be steadily carried out (i.e. shortening the reaction time and enhancing the transformation rate) and make it possible to prepare quaternary ammonium salt (4) in stably high quality, particularly with an industrial advantage.

BEST MODE FOR CARRYING OUT THE INVENTION

Hereinafter, the present invention is further illustrated. The number additionally-described in each "substituent" such as "$C_{1-6}$" means the number of carbons contained therein. For example, "$C_{1-6}$ alkyl" means an alkyl group having 1 to 6 carbon atoms.

The number of substituents defined in an "optionally substituted" or "substituted" group is not limited as long as the substitution is possible, and the number may be one or more. Each substituent used herein may be applied as a part of other substituent or a substituent of other substituent, unless otherwise indicated.

The term "halogen atom" used herein includes, for example, fluorine atom, chlorine atom, bromine atom and iodine atom, and preferably fluorine atom or chlorine atom.

The term "$C_{1-6}$ alkyl group" used herein means a straight or branched chain saturated hydrocarbon group having 1-6 carbon atoms, and the preferable one is "$C_{1-4}$ alkyl group". The "$C_{1-6}$ alkyl group" includes, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{3-7}$ cycloalkyl group" used herein means a cyclic saturated hydrocarbon group having 3-7 carbon atoms, and the preferable one is "$C_{3-6}$ cycloalkyl group". The "$C_{3-7}$ cycloalkyl group" includes, for example, cyclopropyl, cyclobutyl, cyclopentyl, and cyclohexyl.

The term "$C_{6-10}$ aryl group" used herein means an aromatic hydrocarbon group having 6-10 carbon atoms, and the preferable one is "$C_6$ aryl group" (i.e. phenyl). The "$C_{6-10}$ aryl group" includes, for example, phenyl, 1-naphthyl and 2-naphthyl.

The term "$C_{1-6}$ alkoxy group" used herein means a $C_{1-6}$ alkyloxy group, wherein the $C_{1-6}$ alkyl moiety is defined as the above-mentioned "$C_{1-6}$ alkyl", and the preferable one is "$C_{1-4}$ alkoxy group". The "$C_{1-6}$ alkoxy group" includes, for example, methoxy, ethoxy, propoxy, isopropoxy, butoxy, isobutoxy, sec-butoxy, and tert-butoxy.

The term "$C_{3-7}$ cycloalkoxy group" used herein means a $C_{3-7}$ cycloalkyloxy group, wherein the $C_{3-7}$ cycloalkyl moiety is defined as the above-mentioned "$C_{3-7}$ cycloalkyl". The "$C_{3-7}$ cycloalkoxy group" includes, for example, cyclopropyloxy, cyclobutyloxy, cyclopentyloxy, and cyclohexyloxy.

The "$C_{6-10}$ aryl" moiety in the term "$C_{6-10}$ aryloxy group" used herein is defined as the above-mentioned "$C_{6-10}$ aryl", and the preferable "$C_{6-10}$ aryloxy group" is "$C_6$ aryloxy" (i.e. phenyloxy). The "$C_{6-10}$ aryloxy group" includes, for example, phenoxy, 1-naphthyloxy and 2-naphthyloxy.

The "$C_{1-6}$ alkyl" moiety in the term "$C_{1-6}$ alkylthio group" used herein is defined as the above-mentioned "$C_{1-6}$ alkyl", and the preferable "$C_{1-6}$ alkylthio group" is "$C_{1-4}$ alkylthio group". The "$C_{1-6}$ alkylthio group" includes, for example, methylthio, and ethylthio.

The "$C_{3-7}$ cycloalkyl" moiety in the term "$C_{3-7}$ cycloalkylthio group" used herein is defined as the above-mentioned "$C_{3-6}$ cycloalkyl". The "$C_{3-7}$ cycloalkylthio group" includes, for example, cyclopropylthio, cyclobutylthio, cyclopentylthio, and cyclohexylthio.

The "$C_{6-10}$ aryl" moiety in the term "$C_{6-10}$ arylthio group" used herein is defined as the above-mentioned "$C_{6-10}$ aryl". The "$C_{6-10}$ arylthio group" includes, for example, phenylthio, 1-naphthylthio and 2-naphthylthio.

The "$C_{1-6}$ alkyl" moiety in the term "$C_{1-6}$ alkylsulfonyloxy group" used herein is defined as the above-mentioned "$C_{1-6}$ alkyl", and the preferable "$C_{1-6}$ alkylsulfonyloxy group" is "$C_{1-4}$ alkylsulfonyloxy group". The "$C_{1-6}$ alkylsulfonyloxy group" includes, for example, methylsulfonyloxy, and ethylsulfonyloxy.

The "$C_{6-10}$ aryl" moiety in the term "$C_{6-10}$ arylsulfonyloxy group" used herein is defined as the above-mentioned "$C_{6-10}$ aryl". The "$C_{6-10}$ arylsulfonyloxy group" includes, for example, phenylsulfonyloxy, 1-naphthylsulfonyloxy and 2-naphthylsulfonyloxy.

The "heteroaryl group" used herein includes, for example, a 5- to 10-membered monocyclic or multi-cyclic aromatic group having one or more heteroatoms (e.g. 1 to 4 heteroatoms) independently-selected from nitrogen, sulfur, and oxygen atom. The "multi-cyclic heteroaryl group" preferably includes a bicyclic or tricyclic one, and more preferably a bicyclic one. The "multi-cyclic heteroaryl group" also includes a fused cyclic group of the above-mentioned monocyclic heteroaryl group with the above-mentioned aromatic ring group (e.g. benzene) or non-aromatic ring group (e.g. cyclohexyl). The "heteroaryl group" includes, for example, the following groups.

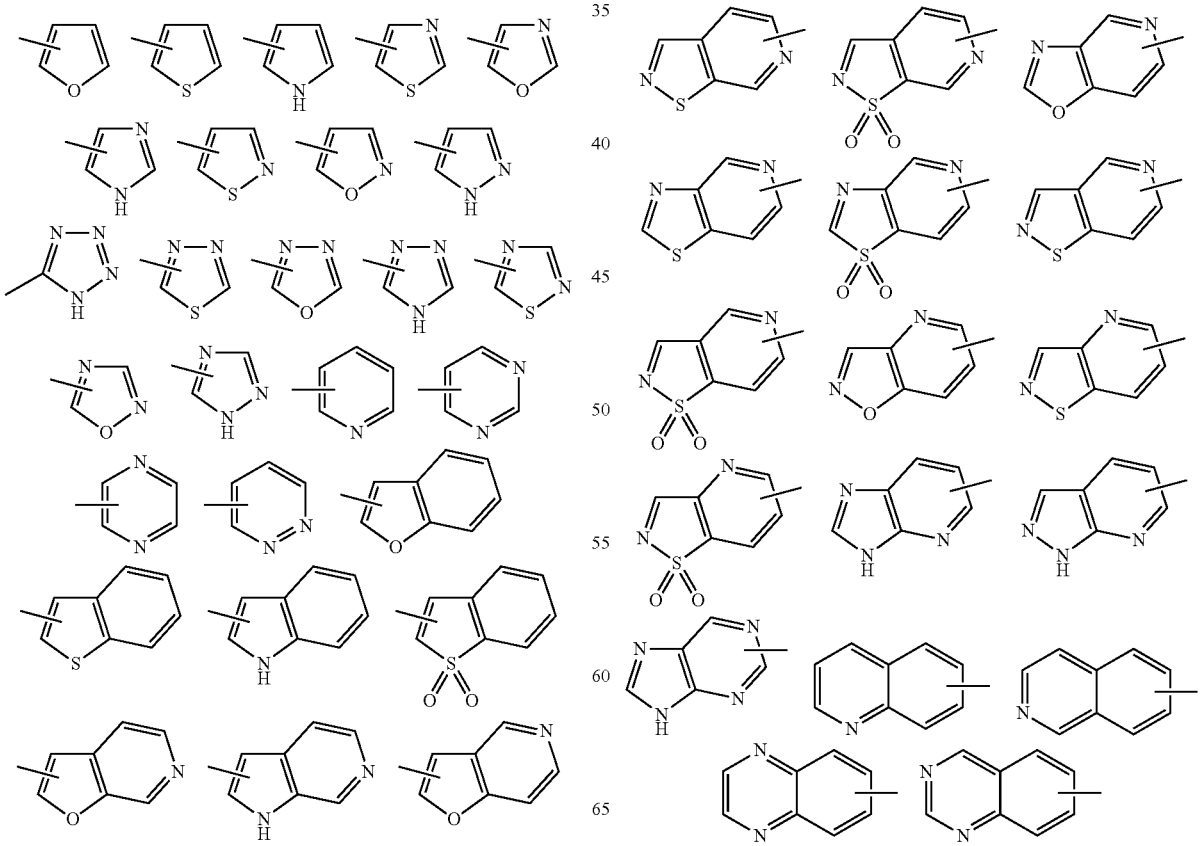

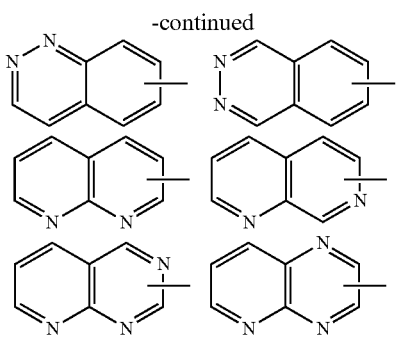

The bond used herein which is connected to the middle of a bond in a ring compound is meant to be attached to any possible position of the ring. For example, the heteroaryl group of the following formula:

means 2-furyl group, or 3-furyl group.

In case that "heteroaryl group" is a multiple-cyclic group, for example, in case of the following group:

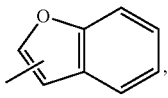

it means 2-benzofuryl group, or 3-benzofuryl group, and additionally, it may mean 4-, 5-, 6- or 7-benzofuryl group. However, in case that a multiple-cyclic heteroaryl group which is composed by fusing an aromatic ring and non-aromatic ring (e.g. piperidine), only the positions in the aromatic ring have the bond. For example, the "multiple-cyclic heteroaryl group" such as the following group:

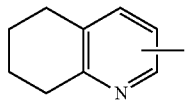

means to be bound on 2-, 3-, or 4-position.

The "heteroaryl" moiety in the term "heteroaryloxy group" used herein is defined as the above-mentioned "heteroaryl group". The "heteroaryloxy group" includes, for example, pyridyloxy.

The "heteroaryl" moiety in the term "heteroarylthio group" used herein is defined as the above-mentioned "heteroaryl group". The "heteroarylthio group" includes, for example, pyridylthio.

The "$C_{5-7}$ cycloalkenyl group" used herein includes a cycloalkenyl group having 5-7 carbon atoms such as cyclopentenyl group, cyclohexenyl group, and cycloheptenyl group.

The "$C_{5-7}$ cycloalkenyloxy group" used herein includes a group composed of the above-mentioned cycloalkenyl group and oxygen atom, such as cyclopentenyloxy group.

The "$C_{5-7}$ cycloalkenylthio group" used herein includes the above-mentioned cycloalkenyloxy group wherein the oxygen atom is replaced by sulfur atom, such as cyclohexylthio group.

The "$C_{1-4}$ alkylene" used herein has 1-4 carbon atoms and includes, for example, methylene, ethylene, and trimethylene.

The "$C_{1-3}$ alkylene" used herein has 1-3 carbon atoms and includes, for example, methylene, ethylene, and trimethylene.

The "hydrocarbon ring" used herein is a cyclic alkane having 3-7 carbon atoms such as $C_{3-7}$ cycloalkane, or a cyclic alkene having 5-7 carbon atoms such as $C_{5-7}$ cycloalkene. The cyclic alkane having 3-7 carbon atoms includes, for example, cyclopropane, cyclobutane, cyclopentane, cyclohexane, cycloheptane. The cyclic alkene having 5-7 carbon atoms includes, for example, cyclopentene, cyclohexene, and cycloheptene.

The "aromatic hydrocarbon ring" used herein means a ring containing the above-mentioned "$C_{6-10}$ aryl" moiety.

The compound of formula (2) (hereinafter, abbreviated as "Compound (2)") includes, for example, 1,4-dibromobutane, 1,4-dichlorobutane, 1,4-diiodobutane, 1,4-dimethanesulfonyloxybutane, 1,4-di(p-toluenesulfonyloxy)-butane, 2-hydroxy-1,3-dibromopropane, 2-hydroxy-1,3-dichloropropane, 2-hydroxy-1,3-dimethanesulfonyloxypropane, 1,2-bis(bromomethyl)cyclohexane, 1,2-bis(methanesulfonyloxymethyl)cyclohexane, 1,2-bis(bromomethyl)cyclopentane, 1,2-bis(methanesulfonyloxymethyl)cyclopentane, 2,3-bis(bromomethyl)-bicyclo[2.2.1]heptane, 2,3-bis(methane-sulfonyloxymethyl)-bicyclo[2.2.1]heptane, 4,5-bis(bromo-methyl)-1-cyclohexene, 4,5-bis(methane-sulfonyloxymethyl)-1-cyclohexene, and 2,3-bis(bromomethyl)-7-oxabicyclo[2.2.1]-hept-5-ene.

The "counteranion" includes, for example, halogen ion (e.g. chlorine ion), sulfate ion, hydrogensulfate ion, phosphate ion, hydrogenphosphate ion, dihydrogenphosphate ion, $C_{1-6}$ alkylsulfonate ion (e.g. methanesulfonate ion), $C_{6-10}$ arylsulfonate ion (e.g. p-toluenesulfonate ion), and hydroxide ion.

The "by-product which is produced by the reaction with potassium carbonate wherein the by-product has a carbonate part therein" (by-product (R)) is all-inclusive term of by-products having at least one carbonate parts therein. In the present specification, these by-products are expressed as "by-product (R)", and the producing rates of by-product (R) in the examples mentioned below are used as an evaluation of the present invention.

In the compound of formula (1) (hereinafter, abbreviated as "Compound (1)"), $C_{1-6}$ alkyl group, $C_{3-7}$ cycloalkyl group, $C_{5-7}$ cycloalkenyl group, $C_{6-10}$ aryl group, and 5- to 10-membered monocyclic or bicyclic heteroaryl group in "$R^1$"; and $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, and 5- to 10-membered monocyclic or bicyclic heteroarylthio group in "$R^2$" may be further optionally substituted with the same or different one to three substituents selected from the group consisting of $C_{1-4}$ alkyl, $C_{1-4}$ alkoxy, $C_{1-4}$ alkylthio and halogen atom.

Compound (1) includes, for example, 4-phenylpiperazine, 4-(2-methoxyphenyl)piperazine, 4-cyclohexylpiperazine, 4-(2-pyridinyl)piperazine, 4-(2-pyrimidinyl)piperazine, 4-(2-quinolyl)piperazine, 4-(4-quinolyl)piperazine, 4-(1,2-benzisothiazol-3-yl)piperazine, 4-(4-fluorophenyl)piperidine, 4-[(4-fluorophenyl)thio]-piperidine, 4-(3-chlorophenyl)piperazine, 4-(1,2-benzisoxazol-3-yl)piperidine, 4-(5-benzofuranyl)piperazine, 4-(1-naphthyl)piperazine, 4-[bis(4-fluorophenyl)methylene]-piperidine, 4-(3-isoquinolyl)piperazine, 4-(8-quinolyl)-piperazine, 4-(7-benzofuranyl)piperazine, and 4-(5-fluoro-1,2-benzisoxazol-3-yl) piperidine. The preferable example is 4-(1,2-benzisothiazol-3-yl)piperazine.

Compound (1) can be prepared according to, for example, JP 63(1988)-83085 A, J. Med. Chem., 28761 (1985), and J. Med. Chem., 32, 1024 (1989). And, Compound (1) may include an addition acid salt thereof (1) such as a hydrochloride and a sulfate thereof.

As Compound (2) used herein, a commercially available compound may be used. In case that Compound (2) has a chiral carbon(s), i.e. it has an optical isomer, the compound herein may be a single optical isomer, a racemic compound thereof, or a mixture of optical isomers in a certain ratio.

A preferable example of Compound (2) includes a compound of the following formula:

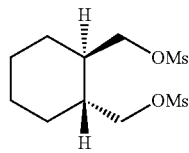

wherein Ms means methanesulfonyl group.

In the reaction between Compound (1) and Compound (2) in the present invention, the amount of Compound (2) used herein is generally 1 mole to 2 mole per one mole of Compound (1). The upper limit amount of Compound (2) used herein is not limited, but, in case that the amount is too much, the process cost increases.

The present invention is directed to the reaction between Compound (1) and Compound (2) using dibasic potassium phosphate with a small amount of water as a base instead of potassium carbonate. The improved process can make the reaction time stabilized and the producing of by-product (R) reduced to prepare a quaternary ammonium salt (4):

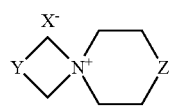

(4)

wherein X, Y and Z are as defined in the above Term 1 (hereinafter, abbreviated as "quaternary ammonium salt (4)") in stably high quality.

The "phosphate" used in the reaction between Compound (1) and Compound (2) includes, for example, an alkali metal phosphate such as potassium phosphate and sodium phosphate; an alkali earth metal salt such as calcium phosphate; and an alkali metal hydrogenphosphate such as dibasic sodium phosphate and dibasic potassium phosphate; preferably dibasic potassium phosphate. Such phosphate may be used alone or as a mixture of two or more kinds of such phosphates. And, such phosphate may be an anhydrous form or a hydrate thereof.

The amount of the phosphate used herein is generally 1.0 mole or more per one mole of Compound (1), and the upper limit amount is not limited, but, in case that the amount is too much, the process cost increases. Accordingly, the amount of the phosphate used is practically 3 mole or less per one mole of Compound (1). And, in case of using an acid addition salt of Compound (1), it is preferable to add an additional appropriate amount of a base to neutralize the acid addition salt. Such base used is generally dibasic potassium phosphate.

The reaction of the present invention is carried out in the coexistence of water, i.e. in the presence of generally 0.01 to 0.1 part by weight, preferably 0.01 to 0.05 part by weight of water per one part by weight of the phosphate. When using a hydrate of dibasic potassium phosphate, the amount of water used herein may be decided considering the water of the hydrate. The water may initially exist in the reaction medium or an appropriate amount of water may be added thereto in mid-course. Or, the water may be added to Compound (1) and/or Compound (2) beforehand.

In addition, the reaction of the present invention may be carried out in the coexistence of a phase-transfer catalyst such as tetra-n-butyl ammonium hydrogen sulfate, tetra-n-butyl ammonium bromide, and benzyl triethyl ammonium chloride. The amount of the phase-transfer catalyst used herein is generally 0.01 to 0.5 mole per one more of the amount of Compound (1).

In case of using an acid addition salt of Compound (1), it is preferable to add an additional appropriate amount of a base to neutralize the acid addition salt.

The solvent used herein includes, for example, an alcohol solvent such as methanol, and ethanol; an aprotic polar solvent such as acetonitrile, and N,N-dimethylformamide; aromatic carbon ring solvent such as toluene, and xylene; which can be used alone or in a mixture of two or more kinds of the solvents and the amount of the solvent used is not limited.

The reaction temperature is generally 60 to 180° C., preferably 90 to 150° C.

After the reaction is completed, for example, the reaction mixture or a part of the reaction mixture can be concentrated and then filtrated to give a mixture of quaternary ammonium salt (4) and a phosphate. In addition, the reaction mixture containing quaternary ammonium salt (4) and a phosphate may be used in the reaction mentioned below without taking out quaternary ammonium salt (4) from the mixture.

Quaternary ammonium salt (4) thus prepared includes, for example, chloride, bromide, iodide, hydroxide, sulfate, hydrogensulfate, phosphate, hydrogenphosphate, dihydrogenphosphate, methanesulfonate, and p-toluenesulfonate of 7-cyclohexyl-2-hydroxy-7-aza-4-azoniaspiro[3.5]-nonane,
8-phenyl-8-aza-5-azoniaspiro[4.5]decane,
8-(2-methoxyphenyl)-8-aza-5-azoniaspiro[4.5]decane,
8-(2-pyridinyl)-8-aza-5-azoniaspiro[4.5]decane,
8-(2-pyrimidinyl)-8-aza-5-azoniaspiro[4.5]decane,
8-(2-quinolyl)-8-aza-5-azoniaspiro[4.5]decane,
8-(4-quinolyl)-8-aza-5-azoniaspiro[4.5]decane,
8-(1,2-benzisothiazol-3-yl)-8-aza-5-azoniaspiro-[4.5]decane,
4'-(1,2-benzisothiazol-3-yl)octahydro-spiro[2H-isoindole-2,1'-piperazinium],
4'-[(4-fluorophenyl)thio]octahydro-spiro[2H-isoindole-2,1'-piperidinium],
4'-(2-pyrimidinyl)octahydro-spiro[2H-isoindole-2,1'-piperazinium],
4'-(4-fluorophenoxy)octahydro-spiro[2H-isoindole-2,1'-piperidinium],
4'-(1,2-benzisoxazol-3-yl)octahydro-spiro[2H-isoindole-2,1'-piperidinium],
4'-(6-fluoro-1,2-benzisoxazol-3-yl)-octahydro-spiro[2H-isoindole-2,1'-piperazinium],
4'-(2-pyridinyl)octahydro-spiro[2H-isoindole-2,1'-piperazinium],
4'-(3-chlorophenyl)octahydro-spiro[2H-isoindole-2,1'-piperazinium], 4'-(5-benzofuranyl)octahydro-spiro[2H-isoindole-2,1'-piperazinium],
4'-(1-naphthyl)octahydro-spiro[2H-isoindole-2,1'-piperazinium],
4'-[bis(4-fluorophenyl)methylene]octahydro-spiro[2H-isoindole-2,1'-piperidinium],
4'-(2-methoxyphenyl)octahydro-spiro[2H-isoindole-2,1'-piperazinium],
4'-(3-isoquinolyl)octahydro-spiro[2H-isoindole-2,1'-piperazinium],
4'-(8-quinolyl)octahydro-spiro[2H-isoindole-2,1'-piperazinium],
4'-(1,2-benzisothiazol-3-yl)tetrahydro-spiro-[cyclopenta[c]pyrrole-2(1H), 1'-piperazinium],
4'-(1,2-benzisothiazol-3-yl)octahydro-spiro[4,7-methano-2H-isoindole-2,1'-piperazinium],
4'-(1,2-benzisothiazol-3-yl)-1,3,3a,4,7,7a-hexahydro-spiro[2H-isoindole-2,1'-piperazinium],
4'-(1,2-benzisothiazol-3-yl)-1,3,3a,4,7,7a-hexahydro-spiro[4,7-epoxy-2H-isoindole-2,1'-piperazinium], or
4'-(7-benzofuranyl)octahydro-spiro[2H-isoindole-2,1'-piperazinium].

By reacting the resulting quaternary ammonium salt (4) and a compound of formula (7):

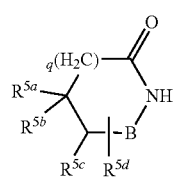

(7)

wherein the symbols are as defined in the above Term 13 (hereinafter, abbreviated as "Compound (7)") in the presence of a solid inorganic base, an imide compound of formula (8):

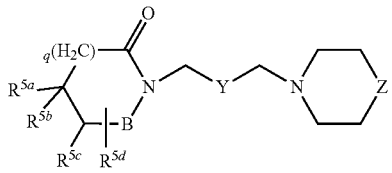

(8)

wherein the symbols are as defined in the above Term 13 (hereinafter, abbreviated as "imide compound (8)") can be prepared.

Compound (7) includes a compound of the following formula (7a):

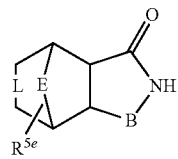

(7a)

wherein -L- is a single or double bond, E is $C_{1-3}$ alkylene optionally substituted with $C_{1-4}$ alkyl or oxygen atom, $R^{5e}$ is hydrogen atom or $C_{1-4}$ alkyl group, and B is as defined in the above formula (7).

Compound (7) includes, for example, succinimide, 2,6-piperidine-dione, 4,4-dimethyl-2,6-piperidine-dione, 8-azaspiro[4.5]decane-7,9-dione, perhydroazepin-2,7-dione, maleimide, phthalimide, tetrahydrophthalimide, cis-1,2-cyclohexane-dicarboximide, trans-1,2-cyclohexane-dicarboximide, cis-1,2-cyclohex-4-ene-dicarboximide, trans-1,2-cyclohex-4-ene-dicarboximide, cis-4-methyl-1,2-cyclohexane-dicarboximide, trans-4-methyl-1,2-cyclohexane-dicarboximide, cis-1,2-dimethyl-1,2-cyclohexane-dicarboximide, trans-1,2-dimethyl-1,2-cyclohexane-dicarboximide, cis-4,5-dimethyl-1,2-cyclohexane-dicarboximide, trans-4,5-dimethyl-1,2-cyclohexane-dicarboximide, cis-3,6-dimethyl-1,2-cyclohexane-dicarboximide, trans-3,6-dimethyl-1,2-cyclohexane-dicarboximide, bicyclo[2.2.1]heptane-2,3-di-exo-carboximide, bicyclo[2.2.1]heptane-2,3-di-endo-carboximide, bicyclo[2.2.1]hept-5-ene-2,3-di-exo-carboximide, bicyclo[2.2.1]hept-5-ene-2,3-di-endo-carboximide, bicyclo[2.2.2]octane-2,3-di-exo-carboximide, bicyclo[2.2.2]octane-2,3-di-endo-carboximide, bicyclo[2.2.2]oct-5-ene-2,3-di-exo-carboximide, bicyclo[2.2.2]oct-5-ene-2,3-di-endo-carboximide, bicyclo[2.2.2]oct-7-ene-2,3-di-exo-carboximide, bicyclo[2.2.2]oct-7-ene-2,3-di-endo-carboximide, hexahydro-4,7-methano-1,2-benzisothiazol-3(2H)-one-1,1-dioxide, 3,6-epoxy-1,2-cyclohexane-dicarboximide, and spiro[bicyclo[2.2.2]octane-2,3'-pyrrolidine]-2',5'-dione.

A preferable example of Compound (7) includes a compound of the following (7b):

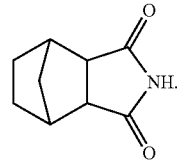

(7b)

Compound (7b) can include its optical isomers, thus the compound used herein may be one of the optical isomers or a mixture of the optical isomers. A preferable example of Compound (7) includes a compound of the following formula:

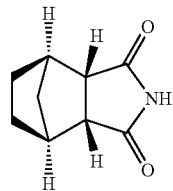 [SMILES: O=C1NC(=O)[C@H]2[C@@H]3CC[C@@H](C3)[C@@H]12]

or a salt thereof.

Compound (7) can be prepared, for example, by reacting a corresponding carboxylic anhydride compound and ammonia (for example, JP-1(1989)-199967 A).

The solid inorganic base (salt) includes, for example, an alkali metal carbonate such as potassium carbonate, and sodium carbonate; an alkali earth metal salt such as calcium carbonate, and magnesium carbonate; and an alkali metal bicarbonate such as sodium bicarbonate, and potassium bicarbonate; preferably an alkali metal carbonate, in particular, potassium carbonate. Such solid inorganic base may be used alone or as a mixture of two or more kinds of bases. And, such solid inorganic bases may be an anhydrous form or a hydrate thereof.

The amount of the solid inorganic base used herein is generally 0.7 mole or more, preferably 0.9 mole or more per one mole of the amount of Compound (1) or quaternary ammonium salt (4). The upper limit amount of the solid inorganic base used herein is not limited, but, in case that the amount is too much, the process cost increases. Accordingly, the practical amount of the solid inorganic base is 3 mole or less, preferably 2.7 mole or less per one mole of the amount of Compound (1) or quaternary ammonium salt (4).

The amount of Compound (7) used herein is generally 0.7 mole or more per one mole of the amount of Compound (1) or quaternary ammonium salt (4). The upper limit amount of Compound (7) used herein is not limited, but, in case that the amount is too much, the process cost increases. Accordingly, the practical amount of Compound (7) is 2.5 mole or less per one mole of the amount of Compound (1) or quaternary ammonium salt (4).

The reaction of the present invention is generally carried out in the presence of a solvent. The solvent used herein includes, for example, aromatic hydrocarbons such as toluene, xylene, mesitylene, chlorobenzene, and dichlorobenzene. The amount of such solvent used herein is generally 3 parts by weight or more, preferably 5 parts by weight or more per one part by weight of the total amount of Compound (1) or quaternary ammonium salt (4). The upper limit amount of the solvent used herein is not limited, but, in case that the amount is too much, the volumetric efficiency is turned down. Accordingly, the practical amount of the solvent is 20 parts by weight or less per one part by weight of the amount of Compound (1) or quaternary ammonium salt (4).

The reaction of the present invention is preferably carried out in the coexistence of water, i.e. in the presence of generally 0.05 to 3 mole, preferably 0.1 to 1.5 mole of water per one mole of the amount of Compound (1) or quaternary ammonium salt (4). When using a hydrate of solid inorganic base, the amount of water used herein may be decided considering the water of the hydrate. The water may initially exist in the reaction medium or an appropriate amount of water may be added thereto in mid-course. Or, the water may be added to Compound (7) and/or quaternary ammonium salt (4) beforehand.

In addition, the reaction of the present invention may be carried out in the coexistence of a phase-transfer catalyst such as tetra-n-butyl ammonium hydrogen sulfate, tetra-n-butyl ammonium bromide, and benzyl triethyl ammonium chloride. The amount of the phase-transfer catalyst used herein is generally 0.01 to 0.5 mole per one mole of the amount of Compound (2) or quaternary ammonium salt (4).

The reaction temperature is generally 80 to 180° C., preferably 95 to 150° C.

The reaction of quaternary ammonium salt (4) and Compound (7) is generally carried out by contacting and mixing quaternary ammonium salt (4), Compound (7) and a solid inorganic base, and the addition order of the substances is not limited. The solid inorganic base may be added thereto in separated amounts or in a lump, but it is preferable in a lump.

The reaction mixture containing imide compound (8) is obtained after the reaction, and the mixture can be treated by adding water thereto, mixing it, standing still in a whole, separating it with a separating funnel, optionally treating the organic layer with active carbon, and concentrating the organic layer to give imide compound (8). Alternatively, imide compound (8) can be obtained as a crystal by cooling the above-mentioned organic layer or the partially-concentrated organic layer, or adding another solvent which is comparatively insoluble for imide compound (8) to the organic layer. The solvent which is comparatively insoluble for imide compound (8) includes, for example, an aliphatic hydrocarbon solvent such as pentane, hexane, and heptane, and an alcohol solvent such as methanol, ethanol, and isopropanol.

In addition, imide compound (8) can be also obtained from the reaction mixture containing imide compound (8) by removing out insoluble precipitates with a filter and concentrating the filtrate. Further, imide compound (8) can be obtained as a crystal by cooling the reaction mixture or the partially-concentrated reaction mixture, or adding another solvent which is comparatively insoluble for imide compound (8) to the organic layer.

The obtained imide compound (8) may be further purified by a conventional purification such as recrystallization and chromatography. In addition, imide compound (8) can be obtained as an inorganic acid addition salt such as hydrochloride, sulfate, hydrobromide, and phosphate; or an organic acid addition salt such as acetate, oxalate, citrate, malate, tartrate, maleate, and fumarate.

The imide compound (8) prepared herein includes, for example,

2-[4-(4-phenyl-1-piperazinyl)butyl]hexahydro-1H-isoindole-1,3(2H)-dione,

2-[4-(4-phenyl-1-piperazinyl)butyl]hexahydro-4,7-methano-1H-isoindole-1,3(2H)-dione, 2-[4-[4-(2-methoxyphenyl)-1-piperazinyl]butyl]-hexahydro-1H-isoindole-1,3(2H)-dione, 2-[4-[4-(2-methoxyphenyl)-1-piperazinyl]butyl]-hexahydro-4,7-methano-1H-isoindole-1,3(2H)-dione, 2-[[2-[[4-(1,2-benzisothiazol-3-yl)-1-piperazinyl]-methyl]cyclohexyl]methyl]hexahydro-4,7-methano-1H-isoindole-1,3(2H)-dione (2-[2-[4-(1,2-benzisothiazol-3-yl)-piperazin-1-ylmethyl]cyclohexylmethyl]hexahydro-4,7-methano-2H-isoindole-1,3-dione), 2-[[2-[[4-(1,2-benzisothiazol-3-yl)-1-piperazinyl]-methyl]cyclohexyl]methyl]hexahydro-4,7-methano-1,2-benzisothiazole-3(2H)-one-1,1-dioxide, 2-[[2-[[4-(1,2-benzisothiazol-3-yl)-1-piperazinyl]-methyl]cyclohexyl]methyl]hexahydro-1H-isoindole-1,3(2H)-dione, 2-[[2-[[4-(2-pyrimidinyl)-1-piperazinyl]methyl]-cyclohexyl]methyl]hexahydro-4,7-methano-1H-isoindole-1,3(2H)-dione, 2-[[2-[[4-(1,2-benzisothiazol-3-yl)-1-piperazinyl]-methyl]cyclohexyl]methyl]-3a,4,7,7a-tetrahydro-1H-isoindole-1,3(2H)-dione, 8-[[2-[[4-(1,2-benzisothiazol-3-yl)-1-piperazinyl]-methyl]cyclohexyl]methyl]-8-azaspiro[4,5]decane-7,9-dione, 1-[[2-[[4-(1,2-benzisothiazol-3-yl)-1-piperazinyl]-methyl]cyclohexyl]methyl]-4,4-dimethyl-2,6-piperidine-dione, 2-[[2-[[4-(1,2-benzisothiazol-3-yl)-1-piperazinyl]-methyl]cyclohexyl]methyl]hexahydro-4,7-epoxy-1H-isoindole-1,3(2H)-dione, 1'-[[2-[[4-(1,2-benzisothiazol-3-yl)-1-piperazinyl]-methyl]cyclohexyl]methyl]-spiro[bicyclo[2.2.2]octane-2,3'-pyrrolidine]-2',5'-dione, 2-[[2-[[4-(1,2-benzisothiazol-3-yl)-1-piperazinyl]-methyl]cyclohexyl]methyl]hexahydro-3a,7a-dimethyl-1H-isoindole-1,3(2H)-dione, 2-[[2-[[4-(1,2-benzisothiazol-3-yl)-1-piperazinyl]-methyl]cyclohexyl]methyl]-3a,4,7,7a-tetrahydro-4,7-ethano-1H-isoindole-1,3(2H)-dione, 2-[[2-[[4-(1,2-benzisothiazol-3-yl)-1-piperazinyl]-methyl]cyclohexyl]methyl]hexahydro-4,7-ethano-1H-isoindole-1,3(2H)-dione, 2-[[2-[[4-(1,2-benzisothiazol-3-yl)-1-piperazinyl]-methyl]cyclohexyl]methyl]-1H-isoindole-1,3(2H)-dione,
2-[[2-[[4-(1,2-benzisothiazol-3-yl)-1-piperazinyl]-methyl]cyclohexyl]methyl]-4,5,6,7-tetrahydro-1H-isoindole-1,3(2H)-dione,
2-[[2-[[4-[(4-fluorophenyl)thio]-1-piperidyl]-methyl]cyclohexyl]methyl]hexahydro-4,7-methano-1H-isoindole-1,3(2H)-dione,
2-[[2-[[4-[(4-fluorophenyl)thio]-1-piperidyl]-methyl]cyclohexyl]methyl]hexahydro-1H-isoindole-1,3(2H)-dione,
2-[[2-[[4-(4-fluorophenoxy)-1-piperidyl]methyl]-cyclohexyl]methyl]hexahydro-4,7-methano-1H-isoindole-1,3(2H)-dione,
2-[[2-[[4-(4-fluorophenoxy)-1-piperidyl]methyl]-cyclohexyl]methyl]hexahydro-1H-isoindole-1,3(2H)-dione,
2-[[2-[[4-(1,2-benzisoxazol-3-yl)-1-piperidyl]-methyl]cyclohexyl]methyl]hexahydro-4,7-methano-1H-isoindole-1,3(2H)-dione,
2-[[2-[[4-(1,2-benzisoxazol-3-yl)-1-piperidyl]-methyl]cyclohexyl]methyl]hexahydro-1H-isoindole-1,3(2H)-dione,
2-[[2-[[4-(6-fluoro-1,2-benzisoxazol-3-yl)-1-piperidyl]methyl]cyclohexyl]methyl]hexahydro-4,7-methano-1H-isoindole-1,3(2H)-dione,
2-[[2-[[4-(6-fluoro-1,2-benzisoxazol-3-yl)-1-piperidyl]methyl]cyclohexyl]methyl]hexahydro-1H-isoindole-1,3(2H)-dione,
2-[[2-[[4-(2-pyridinyl)-1-piperazinyl]methyl]-cyclohexyl]methyl]hexahydro-4,7-methano-1H-isoindole-1,3(2H)-dione,
2-[[2-[[4-(2-pyridinyl)-1-piperazinyl]methyl]-cyclohexyl]methyl]hexahydro-1H-isoindole-1,3(2H)-dione,
2-[[2-[[4-(2-pyrimidinyl)-1-piperazinyl]methyl]-cyclohexyl]methyl]hexahydro-4,7-methano-1H-isoindole-1,3(2H)-dione,
2-[[2-[[4-(2-pyrimidinyl)-1-piperazinyl]methyl]-cyclohexyl]methyl]hexahydro-1H-isoindole-1,3(2H)-dione,
2-[[2-[[4-(3-chlorophenyl)-1-piperazinyl]methyl]-cyclohexyl]methyl]hexahydro-4,7-methano-1H-isoindole-1,3(2H)-dione,
2-[[2-[[4-(3-chlorophenyl)-1-piperazinyl]methyl]-cyclohexyl]methyl]hexahydro-1H-isoindole-1,3(2H)-dione,
2-[[2-[[4-(5-benzofuranyl)-1-piperazinyl]methyl]-cyclohexyl]methyl]hexahydro-4,7-methano-1H-isoindole-1,3(2H)-dione,
2-[[2-[[4-(5-benzofuranyl)-1-piperazinyl]methyl]-cyclohexyl]methyl]hexahydro-1H-isoindole-1,3(2H)-dione,
2-[[2-[[4-(1-naphthyl)-1-piperazinyl]methyl]cyclohexyl]methyl]hexahydro-4,7-methano-1H-isoindole-1,3(2H)-dione,
2-[[2-[[4-(1-naphthyl)-1-piperazinyl]methyl]cyclohexyl]methyl]hexahydro-1H-isoindole-1,3(2H)-dione,
2-[[2-[[4-[bis(4-fluorophenyl)methylene]-1-piperidyl]methyl]cyclohexyl]methyl]hexahydro-4,7-methano-1H-isoindole-1,3(2H)-dione,
2-[[2-[[4-[bis(4-fluorophenyl)methylene]-1-piperidyl]methyl]cyclohexyl]methyl]hexahydro-1H-isoindole-1,3(2H)-dione,
2-[[2-[[4-(2-methoxyphenyl)-1-piperazinyl]methyl]-cyclohexyl]methyl]hexahydro-4,7-methano-1H-isoindole-1,3(2H)-dione,
2-[[2-[[4-(2-methoxyphenyl)-1-piperazinyl]methyl]-cyclohexyl]methyl]hexahydro-1H-isoindole-1,3(2H)-dione,
2-[[2-[[4-(3-isoquinolyl)-1-piperazinyl]methyl]-cyclohexyl]methyl]hexahydro-4,7-methano-1H-isoindole-1,3(2H)-dione,
2-[[2-[[4-(3-isoquinolyl)-1-piperazinyl]methyl]-cyclohexyl]methyl]hexahydro-1H-isoindole-1,3(2H)-dione,
2-[[2-[[4-(8-quinolyl)-1-piperazinyl]methyl]cyclohexyl]methyl]hexahydro-4,7-methano-1H-isoindole-1,3(2H)-dione,
2-[[2-[[4-(8-quinolyl)-1-piperazinyl]methyl]-cyclohexyl]methyl]hexahydro-1H-isoindole-1,3(2H)-dione,
2-[[2-[[4-(1,2-benzisothiazol-3-yl)-1-piperazinyl]-methyl]cyclopentyl]methyl]hexahydro-4,7-methano-1H-isoindole-1,3(2H)-dione,
2-[[2-[[4-(1,2-benzisothiazol-3-yl)-1-piperazinyl]-methyl]cyclopentyl]methyl]hexahydro-1H-isoindole-1,3(2H)-dione,
2-[[3-[[4-(1,2-benzisothiazol-3-yl)-1-piperazinyl]-methyl]bicyclo[2.2.1]hept-2-yl]methyl]hexahydro-4,7-methano-1H-isoindole-1,3(2H)-dione,
2-[[3-[[4-(1,2-benzisothiazol-3-yl)-1-piperazinyl]-methyl]bicyclo[2.2.1]hept-2-yl]methyl]hexahydro-1H-isoindole-1,3(2H)-dione,
2-[[2-[[4-(7-benzofuranyl)-1-piperazinyl]methyl]-cyclohexyl]methyl]hexahydro-4,7-methano-1H-isoindole-1,3(2H)-dione,
2-[[2-[[4-(7-benzofuranyl)-1-piperazinyl]methyl]-cyclohexyl]methyl]hexahydro-1H-isoindole-1,3(2H)-dione,
2-[[3-[[4-(1,2-benzisothiazol-3-yl)-1-piperazinyl]-methyl]-7-oxabicyclo[2.2.1]hept-5-ene-2-yl]methyl]-hexahydro-4,7-methano-1H-isoindole-1,3(2H)-dione,
2-[[3-[[4-(1,2-benzisothiazol-3-yl)-1-piperazinyl]-methyl]-7-oxabicyclo[2.2.1]hept-5-ene-2-yl]methyl]-hexahydro-1H-isoindole-1,3(2H)-dione,
2-[[6-[[4-(1,2-benzisothiazol-3-yl)-1-piperazinyl]-methyl]-3-cyclohexen-1-yl]methyl]hexahydro-4,7-methano-1H-isoindole-1,3(2H)-dione, and
2-[[6-[[4-(1,2-benzisothiazol-3-yl)-1-piperazinyl]-methyl]-3-cyclohexen-1-yl]methyl]hexahydro-1H-isoindole-1,3(2H)-dione.

In case that the optically active compound (7) and/or the optically active quaternary ammonium salt (4) are used in the reaction, the optically active corresponding imide compound (8) can be obtained.

In addition, the present invention includes the following process:

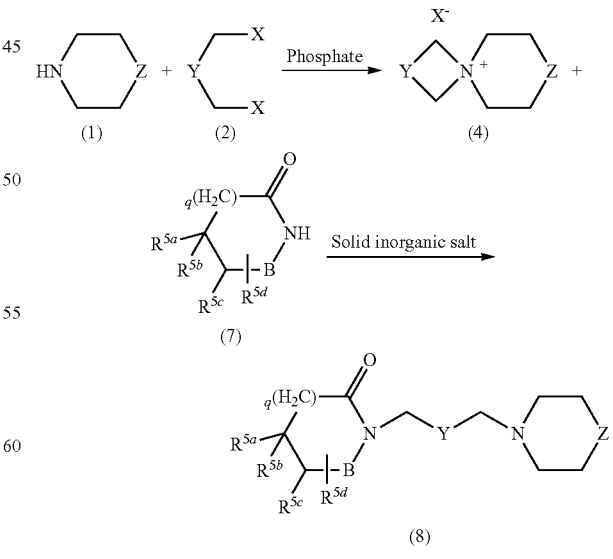

wherein the symbols described in the scheme are as defined in Terms 1 and 13 mentioned above.

EXAMPLE

Hereinafter, the present invention is illustrated in more detail by the following Example and Comparative Example, but it should not be construed to be limited thereto. The analyses in the examples were done by high-performance liquid chromatography (LC).

Example 1

To a mixed solution of 4-(1,2-benzisothiazol-3-yl)piperazine [Compound (A)] (20.0 g, 91.2 mmol), (1R,2R)-1,2-bis(methanesulfonyloxymethyl)cyclohexane [Compound (B)] (32.9 g, 109.5 mmol), and toluene (280 g) were added dibasic potassium phosphate (47.7 g, 273.9 mmol), water (1.4 g, 77.8 mmol) and tetra-n-butyl ammonium hydrogen sulfate (1.2 g, 3.5 mmol). The mixture was stirred under reflux for 15 hours (water (0.5 g) was added in mid-course) to give a reaction mixture containing 4'-(1,2-benzisothiazol-3-yl)-(3aR,7aR)-octahydro-spiro[2H-isoindole-2,1'-piperazinium]methanesulfonate [Compound (C)].

Example 2

To the reaction mixture containing Compound (C) which was obtained in the above Example 1 were added (3aR,4S,7R,7aS)-hexahydro-4,7-methano-2H-isoindole-1,3-dione [Compound (D)] (22.6 g, 136.8 mmol), potassium carbonate (15.1 g, 109.3 mmol) and toluene (44 g). Then, the toluene (44 g) was distilled out from the mixture, water (0.82 g) was added thereto, and the resulting mixture was reacted under reflux for 8 hours. Then, the reaction mixture was cooled to room temperature, and water (400 g) was added to the mixture. The mixture was separated with a separating funnel, and the toluene layer was washed with 2.3% (W/W) brine (350 g). Further, active carbon (1.8 g) was added to the toluene solution, and the mixture was stirred for 1 hour. The active carbon was removed by filtration to give a toluene solution containing (3aR,4S,7R,7aS)-2-{(1R,2R)-2-[4-(1,2-benzisothiazol-3-yl) piperazin-1-ylmethyl]cyclohexylmethyl}hexahydro-4,7-methano-2H-isoindole-1,3-dione (2-[[(1R,2R)-2-[[4-(1,2-benzisothiazol-3-yl)-1-piperazinyl]methyl]cyclohexyl]methyl]hexahydro-(3aS,4R,7S,7aR)-4,7-methano-1H-isoindole-1,3(2H)-dione) [Compound (E)] (341.4 g). The yield of Compound E was 94.3% The yield of Compound (E) was calculated based on the analytical result that the content of the compound in the toluene solution was 12.4% (w/w) (which was calculated by LC absolute calibration curve method). And, the production rate of by-product (R) was 0.013% (which was calculated with the following formula (a)).

$$\text{Production rate of by-product derived from carbonate} = \frac{\text{Total } LC \text{ area of by-product derviced from carboante}}{\text{Total } LC \text{ area of detected peaks except solvent}} \times 100 \quad (a)$$

Example 3

To a mixture of Compound (A) (20.0 g, 91.2 mmol), Compound (B) (32.9 g, 109.5 mmol) and toluene (280 g) was added dibasic potassium phosphate (23.8 g, 136.6 mmol), water (0.95 g, 52.8 mmol) and tetra-n-butyl ammonium hydrogen sulfate (1.2 g, 3.5 mmol). The mixture was stirred under reflux for 14 hours to give a reaction mixture containing Compound (C).

Example 4

To the reaction mixture containing Compound (C) which was obtained in the above Example 3 were added Compound (D) (22.6 g, 136.8 mmol) and potassium carbonate (15.1 g, 109.3 mmol), and the mixture was stirred under reflux for 6 hours. Then, the reaction mixture was cooled to room temperature, and water (400 g) was added to the mixture. The mixture was separated with a separating funnel, and the toluene layer was washed with 2.3% (W/W) brine (350 g). Further, active carbon (1.8 g) was added to the toluene solution, and the mixture was stirred for 1.5 hours. The active carbon was removed by filtration to give a toluene solution containing Compound (E) (415.4 g). The yield of Compound E was 88.6%. The yield of Compound (E) was calculated based on the analytical result that the content of the compound in the toluene solution was 9.6% (w/w) (which was calculated by LC absolute calibration curve method). And, the production rate of by-product (R) was 0.019% (which was calculated with the above formula (a)).

Comparative Example 1

To a mixture of Compound (A) (140.1 kg, 638.8 mol), Compound (B) (230.3 kg, 766.7 mol) and toluene (2272 kg) was added potassium carbonate (53.0 kg, 383.5 mol), the toluene (312 kg) was removed by heating, and then the mixture was reflux-dehydrated for 5 hours. Then, the reaction mixture was cooled to 70° C. or lower, and potassium carbonate (26.5 kg, 191.7 mol) and tetra-n-butyl ammonium hydrogen sulfate (8.7 kg, 25.6 mol) were added to the mixture. The mixture was refluxed for 10 hours to give the reaction mixture containing Compound (C).

Comparative Example 2

To the reaction mixture containing Compound (C) which was obtained in the above Comparative Example 1 were added toluene (309.6 kg), Compound (D) (158.3 kg, 958.3 mol) and potassium carbonate (105.9 kg, 766.2 mol), and then the toluene (308 kg) was removed by heating. Then, the reaction mixture was cooled to 70° C. or lower, and water (5.7 kg) was added to the mixture. The mixture was refluxed for 4 hours. The reaction mixture was cooled, and water (2819 kg) was added to the mixture. The mixture was separated with a separating funnel, and the toluene layer was washed with 2.3% (w/w) brine (2466 kg). Further, active carbon (12.5 kg) was added to the toluene solution, and the mixture was stirred for 1 hour. The active carbon was removed by filtration and washed with toluene to give a toluene solution containing Compound (E) (2562 kg). The yield of Compound (E) was 87.7%. The yield of Compound (E) was calculated based on the analytical result that the content of the compound in the toluene solution was 10.8% (w/w) (which was calculated by LC absolute calibration curve method). And, the production rate of by-product (R) was 9.83% (which was calculated with the above formula (a)).

Comparative Example 3

To a mixture of Compound (A) (90.0 kg, 410.4 mol), Compound (B) (147.9 kg, 492.4 mol) and toluene (1460 kg)

were added potassium carbonate (34.0 kg, 246.0 mol) and water (636 g), the toluene (298 kg) was removed by heating, and then the mixture was reflux-dehydrated for 34 hours. Then, the reaction mixture was cooled to 70° C. or lower, and potassium carbonate (17.0 kg, 123.0 mol) and tetra-n-butyl ammonium hydrogen sulfate (5.6 kg, 16.5 mol) were added to the mixture. The mixture was refluxed for 12 hours to give the reaction mixture containing Compound (C). And, the production rate of by-product (R) was 3.02% (which was calculated with the above formula (a)).

Comparative Example 4

To the reaction mixture containing Compound (C) which was obtained in the above Comparative Example 3 were added toluene (198 kg), Compound (D) (101.7 kg, 615.7 mol) and potassium carbonate (68.1 kg, 492.7 mol), and then the toluene (198 kg) was removed by heating. Then, the reaction mixture was cooled to 70° C. or lower, and water (3.7 kg) was added to the mixture. The mixture was refluxed for 3 hours. The reaction mixture was cooled, and water (1803 kg) was added to the mixture. The mixture was separated with a separating funnel, and the toluene layer was washed with 2.3% (w/w) brine (1578 kg). Further, active carbon (8.0 kg) was added to the toluene solution, and the mixture was stirred for 1 hour. The active carbon was removed by filtration and washed with toluene to give a toluene solution containing Compound (E) (1625 kg). The yield of Compound (E) was 90.1%. The yield of Compound (E) was calculated based on the analytical result that the content of the compound in the toluene solution was 11.2% (w/w) (which was calculated by LC absolute calibration curve method). And, the production rate of by-product (R) was 3.08% (which was calculated with the above formula (a)).

Each reaction time, product yield, and by-product yield in the above examples and comparative examples is shown in the following table.

|  | Process | Compound (B) (mol) | dibasic potassium phosphate (mol) | Potassium carbonate (mol) | Reaction time (hr) | Product yield (%) | By-product (R) (%) |
|---|---|---|---|---|---|---|---|
| Example 1 | (A) | 1.2 | 3.0 | — | 15 |  |  |
| Example 2 | (B) |  | — | 1.2 | 8 | 94 | 0.013 |
| Example 3 | (A) | 1.2 | 1.5 | — | 14 |  |  |
| Example 4 | (B) |  | — | 1.2 | 6 | 89 | 0.019 |
| Comparative Example 1 | (A) | 1.2 | — | 0.9 | 15 |  |  |
| Comparative Example 2 | (B) |  | — | 1.2 | 4 | 88 | 9.83 |
| Comparative Example 3 | (A) | 1.2 | — | 0.9 | 46 |  | 3.02 |
| Comparative Example 4 | (B) |  | — | 1.2 | 3 | 90 | 3.08 |

Process (A): Compound (A) + Compound (B) --> quaternary ammonium salt (C)
Process (B): quaternary ammonium salt (C) + Compound (D) --> imide compound (E)

According to the results of Examples 1 and 3, the process of the present invention can make the reaction time for preparing quaternary ammonium salt (4) shortened, i.e. the reaction times in all the examples could be steadily shortened in 15 hours. In addition, the production of by-product (R) could be drastically held down by the present invention. Accordingly, the process of the present invention is an industrially useful manufacturing method which is also for practical preparation.

INDUSTRIAL APPLICABILITY

The process of the present invention is a process for preparing quaternary ammonium salt (4) in steady reaction time and in steady quality, thus it has some merits, in particular for the industrial purpose.

The invention claimed is:
1. A process for preparing a quaternary ammonium salt of formula (4):

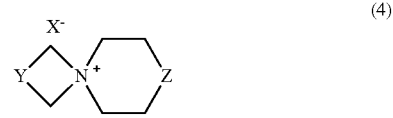

(4)

wherein
X is halogen atom, $C_{1-6}$ alkylsulfonyloxy group, or $C_{6-10}$ arylsulfonyloxy group, and $X^-$ is a counteranion thereof,
Y is a substituent of the following formula (3a) or (3b):

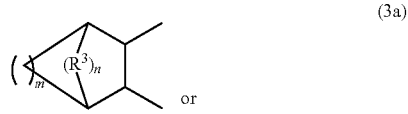

(3a)

or

(3b)

wherein $R^3$ is independently methylene or oxygen atom; $R^4$ is independently $C_{1-6}$ alkyl group, $C_{1-6}$ alkoxy group, or hydroxy group; m and n are independently 0, 1, 2, or 3; and p is 1 or 2, and Z is =N—$R^1$ or =CH—$R^2$ wherein $R^1$ is $C_{1-6}$ alkyl group, $C_{3-7}$ cycloalkyl group, $C_{5-7}$ cycloalkenyl group, $C_{6-10}$ aryl group, or 5- to 10-membered monocyclic or bicyclic heteroaryl group; $R^2$ is $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, or 5- to 10-membered monocyclic or bicyclic heteroarylthio group, comprising reacting a compound of formula (1):

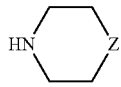

(1)

wherein Z is as defined above with 1 to 2 mole of a compound of formula (2):

(2)

wherein X is independently selected from the above-defined ones, and Y is as defined above, per one mole of the compound of formula (1)

in the presence of 1 to 5 mole of a phosphate per one mole of the compound of formula (1) and 0.01 to 0.1 part by weight of water per one part by weight of the phosphate.

2. The process of claim 1 wherein X is independently $C_{1-6}$ alkylsulfonyloxy group, or $C_{6-10}$ arylsulfonyloxy group.

3. The process of claim 2 wherein X is methanesulfonyloxy group.

4. The process of claim 1 wherein Y is the substituent of formula (3a).

5. The process of claim 4 wherein m is 2 and n is 0.

6. The process of claim 1 wherein Z is =N—$R^1$.

7. The process of claim 6 wherein $R^1$ is 5- to 10-membered monocyclic or bicyclic heteroaryl group.

8. The process of claim 7 wherein $R^1$ is 1,2-benzisothiazol-3-yl.

9. The process of claim 1 wherein the phosphate is dibasic potassium phosphate.

10. The process of claim 1 wherein the phosphate is 1 to 3 mole per one mole of the compound of formula (1).

11. The process of claim 1 wherein the amount of water is 0.01 to 0.05 part by weight per one part by weight of the phosphate.

12. A process for preparing a quaternary ammonium salt of formula (4a):

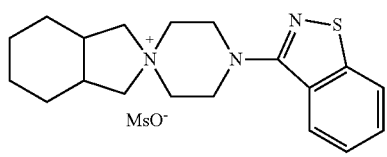

(4a)

comprising reacting a compound of formula (1a):

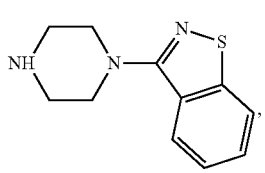

(1a)

with 1 to 2 mole of a compound of formula (2a):

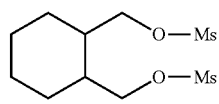

(2a)

per one mole of the compound of formula (1a) in the presence of 1 to 5 mole of a phosphate per one mole of the compound of formula (1a) and 0.01 to 0.1 part by weight of water per one part by weight of the phosphate.

13. A process for preparing a compound of formula 8:

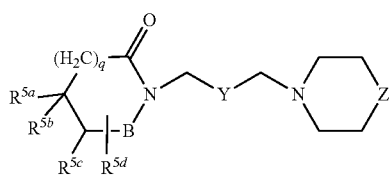

(8)

or an acid addition salt thereof
wherein
B is a carbonyl group or a sulfonyl group,
$R^{5a}$, $R^{5b}$, $R^{5c}$, and $R^{5d}$ are independently a hydrogen atom or a $C_{1-4}$ alkyl group, alternatively $R^{5a}$ and $R^{5b}$, or $R^{5a}$ and $R^{5c}$ may be taken together to form a hydrocarbon ring, or $R^{5a}$ and $R^{5c}$ may be taken together to form an aromatic hydrocarbon ring, wherein the hydrocarbon ring may be bridged with $C_{1-4}$ alkylene or oxygen atom wherein the $C_{1-4}$ alkylene and the hydrocarbon ring may be substituted with at least one $C_{1-4}$ alkyl,
q is 0 or 1, and
Y is a substituent of the following formula (3a) or (3b):

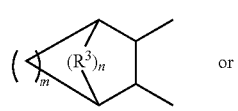

(3a)

or

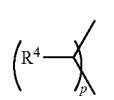

(3b)

wherein $R^3$ is independently methylene or oxygen atom; $R^4$ is independently $C_{1-6}$ alkyl group, $C_{1-6}$ alkoxy group, or hydroxyl group; m and n are independently 0, 1, 2, or 3; and p is 1 or 2, and
Z is =N—$R^1$ or =CH—$R^2$ wherein $R^1$ is $C_{1-6}$ alkyl group, $C_{3-7}$ cycloalkyl group, $C_{5-7}$ cycloalkenyl group, $C_{6-10}$ aryl group, or 5- to 10-membered monocyclic or bicyclic heteroaryl group; $R^2$ is $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{6-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, or 5- to 10-membered monocyclic or bicyclic heteroarylthio group, comprising the following steps (i) and (ii):

step (i)

a process for preparing a quaternary ammonium salt of formula (4):

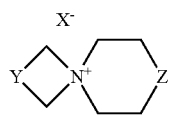

(4)

wherein X is halogen atom, $C_{1-6}$ alkylsulfonyloxy group, or $C_{6-10}$ arylsulfonyloxy group, and Y and Z are as defined above, comprising reacting a compound of formula (1):

(1)

wherein Z is as defined above
with 1 to 2 mole of a compound of formula (2):

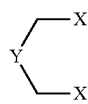

(2)

wherein X and Y are defined above, per one mole of the compound of formula (1)

in the presence of 1 to 5 mole of a phosphate per one mole of the compound of formula (1) and 0.01 to 0.1 part by weight of water per one part by weight of the phosphate; and step (ii)

a process for preparing the compound of formula (8)

comprising reacting the quaternary ammonium salt (4) prepared in step (i) with the following compound (7):

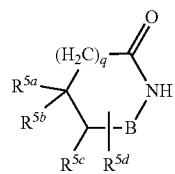

(7)

wherein B, $R^{5a}$, $R^{5b}$, $R^{5c}$, $R^{5d}$ and q are as defined above, in the presence of a solid inorganic base.

14. The process of claim 13 which further comprises the following step (iii) after the reaction of step (ii):

adding a solvent to the product in step (ii) to obtain the compound of formula (8) as a crystal, wherein the solvent is an aliphatic hydrocarbon solvent and/or an alcohol solvent.

15. The process of claim 14 wherein the solvent in step (iii) is an alcohol solvent.

16. The process of claim 15 wherein the alcohol solvent is methanol, ethanol and/or isopropanol.

17. The process of claim 13 wherein the compound of formula (8) is (3aR,4s,7R,7aS)-2-{(1R,2R)-2-[4-(1,2-benisothiazole-3-yl)-piperazin-1-ylmethyl]cyclohexylmethyl]hexahydro-4,7-methano-2H-isoindole-1,3-dione.

18. The process of claim 17 wherein the solid inorganic base in step (ii) is an alkali metal carbonate, alkali earth metal carbonate and/or an alkali metal bicarbonate.

19. The process of claim 18 wherein the solid inorganic base in step (ii) is a potassium carbonate.

20. The process of claim 19 wherein the production rate of by-product (R) in step (ii) is 3% or less, wherein the by-product (R) is produced by the reaction of the unreacted compounds of formula (1) and formula (2) with the potassium carbonate in step (ii), and the by-product (R) has a carbonate part therein.

21. The process of claim 20 wherein the production rate is 0.02% or less.

22. The process of claim 12 wherein the compound of formula (2a) is

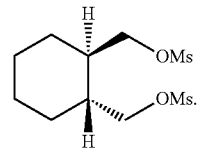 [SMILES: CS(=O)(=O)OC[C@@H]1CCCC[C@H]1COS(C)(=O)=O]

23. The process of claim 13 wherein B is carbonyl group.

24. The process of claim 13 wherein $R^{5a}$ and $R^{5c}$ are taken together to form a hydrocarbon ring which may be bridged with $C_{1-4}$ alkylene, and $R^{5b}$ and $R^{5d}$ are hydrogen atom.

25. The process of claim 24 wherein Compound (7) is the following compound of formula (7b):

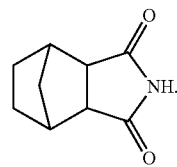

(7b)

26. The process of claim 25 wherein the compound of formula (7b) is

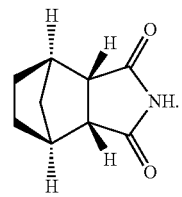 [SMILES: O=C1NC(=O)[C@H]2[C@@H]3CC[C@@H](C3)[C@@H]12]

* * * * *

UNITED STATES PATENT AND TRADEMARK OFFICE
CERTIFICATE OF CORRECTION

PATENT NO.         : 8,586,737 B2                              Page 1 of 1
APPLICATION NO.    : 13/093985
DATED              : November 19, 2013
INVENTOR(S)        : Nobuyuki Ae et al.

It is certified that error appears in the above-identified patent and that said Letters Patent is hereby corrected as shown below:

In the Claims

In claim 13, column 25, lines 3-4, "$C_{6-7}$ cycloalkenylthio group," should read --$C_{5-7}$ cycloalkenylthio group,--.

Signed and Sealed this
Eighteenth Day of August, 2015

Michelle K. Lee
*Director of the United States Patent and Trademark Office*